United States Patent
Muller

(10) Patent No.: US 7,083,350 B2
(45) Date of Patent: Aug. 1, 2006

(54) APPLICATION DEVICE FOR APPLYING A COMPOSITE SUBSTANCE TO A SITE

(75) Inventor: Frank Muller, Feldkirch (AT)

(73) Assignee: Ivoclar Vivadent, AG, Schaan (LI)

( * ) Notice: Subject to any disclaimer, the term of this patent is extended or adjusted under 35 U.S.C. 154(b) by 561 days.

(21) Appl. No.: 10/139,580

(22) Filed: May 6, 2002

(65) Prior Publication Data

US 2002/0170833 A1 Nov. 21, 2002

Related U.S. Application Data

(60) Provisional application No. 60/302,186, filed on Jun. 29, 2001.

(30) Foreign Application Priority Data

May 21, 2001 (DE) .......................... 101 24 819

(51) Int. Cl.
*A46B 11/00* (2006.01)

(52) U.S. Cl. ...................................... 401/126
(58) Field of Classification Search ................ 401/118, 401/119, 123–126, 128–130; 604/1, 2
See application file for complete search history.

(56) References Cited

U.S. PATENT DOCUMENTS

| 3,690,777 | A | | 9/1972 | Costa |
| 4,828,419 | A | * | 5/1989 | Porter et al. ................ 401/126 |
| 5,002,415 | A | | 3/1991 | Gueret |
| 5,088,627 | A | | 2/1992 | Musel |
| 5,096,319 | A | * | 3/1992 | Gueret ....................... 401/126 |
| 5,324,128 | A | | 6/1994 | Gueret |
| 5,392,904 | A | | 2/1995 | Frick et al. |
| 5,655,554 | A | * | 8/1997 | Goldberg .................... 132/314 |
| 5,794,632 | A | * | 8/1998 | Gueret ....................... 132/317 |
| 6,105,761 | A | | 8/2000 | Peuker et al. |
| 6,450,717 | B1 | * | 9/2002 | Salz et al. .................. 401/125 |

FOREIGN PATENT DOCUMENTS

| CH | 358031 | 12/1961 |
| DE | 28 09 646 A1 | 9/1979 |
| DE | 3421823 A1 | 5/1985 |
| DE | 92 18 949 U1 | 7/1996 |
| DE | 200 05 457 U1 | 7/2000 |
| EP | 0 474 319 A2 | 3/1992 |
| EP | 1 103 230 A2 | 5/2001 |
| FR | 2 739 357 A2 | 4/1997 |
| JP | 58-76533 | 5/1983 |
| JP | 2-78389 | 6/1990 |
| JP | 10329862 | 12/1998 |
| WO | WO 95/20497 | 8/1995 |

* cited by examiner

*Primary Examiner*—Justine R. Yu
*Assistant Examiner*—Huyen Le
(74) *Attorney, Agent, or Firm*—Alan S. Korman; John C. Thompson

(57) ABSTRACT

An application device for applying a composite substance onto a site is provided that operably applies a composite substance formed of at least two reaction substances which react with one another. The application device includes a receptacle for receiving a fluid. The receptacle has a support element having a working end on which a reaction substance is supported and the receptacle is operable to guide the one reaction substance into reaction contact with another reaction substance to thereby effect the formation of the composite substance. The receptacle is configured with respect to another receptacle which receives therein a reaction substance such that the receptacle comprises either a shaft portion of a grip or the grip itself of the other receptacle adapted to be gripped by a user in deploying the other receptacle.

7 Claims, 2 Drawing Sheets

APPLICATION DEVICE FOR APPLYING A COMPOSITE SUBSTANCE TO A SITE

CROSS-REFERENCE TO RELATED APPLICATIONS

This application claims foreign priority benefits under 35 U.S.C. §119(a)–(d) from German patent application ser. no. 101 24 819.9 filed May 21, 2001. In addition, this application claims the benefit under 35 U.S.C. §119(e) of U.S. provisional patent application Ser. No. 60/302,186 filed Jun. 29, 2001.

BACKGROUND OF THE INVENTION

The present invention relates to an application device for applying a composite substance to a site.

A conventional application device is disclosed, for example, in DE-U1-9218949. In this application device, a support element is received in a case or sheath having side slots through which a fluid can penetrate, which serves to facilitate the wetting of the support element.

This conventional solution should operate to hinder the unobstructed leakage of fluid in the event, for example, that the application device is tipped. In this connection, sealing surfaces are provided between the slot and the application element.

A conventional solution of this type may serve a purpose in connection with the field of cosmetic products. In connection with the field of dental products, however, a precise application of an application element is important. Even if relatively small holes in the slot are provided as disclosed in DE-U1-9218949, which, in accordance with that disclosure, should exercise a certain protective effect, it is not foreclosed that fluid penetrates inadvertently and that the application element is already in a mixed condition prior to the actual wetting operation in which the application element is wetted with the reaction substance.

Numerous other application apparatus are known. For example, an application element has been proposed which is maintained in a submerged condition in a fluid and the pushing down of the receptacle holding the fluid permits an inflow of an additional fluid in the manner of an overflow, in order to thereby place in readiness the mixture which is to be applied. Unfortunately, this solution requires to be sure two separate sealing systems, so that a not inconsiderable effort is required. The need for a multitude of sealing bands necessarily involves a correspondingly large susceptibility to unhygienic conditions and positional instability.

It is further known, in this connection, to provide a membrane disposed between two chambers which each receive a fluid, with the membrane being destroyed in a targeted manner by a sharpened pin which is actuated to destroy the membrane by compression of an inner chamber. This solution requires a particular configuration of the sharp pin, if it is to be reliably ensured that a collision between the sharpened pin and the application element is prevented.

It is further known to mix reaction capable substances such as, for example, a composite for teeth filling, with a base element having a peroxide coating or, respectively, to mix the reaction capable substance with the composite with a peroxide coated spatula. This type of mixing has the disadvantage that a homogeneous mixing with the substantially viscous composite material must be completely utilized.

It is further known, from DE-PS 4315920, to provide a mixing capsule for dental material, the mixing capsule having a cylinder which is provided with a plunger in order to make possible a targeted dispensing of the activated material. This solution permits up to two fluid components and a powder component to be maintained in spaced apart relationship in readiness and to mix, as necessary, that is, immediately before the application, the components with one another.

However, the application of more than three components, as well as the application of a plurality of components one after the other, on the site which is to be treated is not possible with the heretofore known application apparatus.

A further problem with single dose units is the fact that very different amounts of the required components are needed in accordance with the respective size of the site to be handled. In accordance with the concept of single dose units, the unused portion, which can comprise, indeed, up to 90% of the total amount, is then thrown away. From the prospective of cost effectiveness, this is not desired and dentists tend to use the component in bundles and to mix the components in such a manner. Such self-mixing, however, requires a corresponding degree of experience to ensure, on the one hand, a good mixing of the components and, on the other hand, to place in readiness the application amounts in their proper relationship to one another.

SUMMARY OF THE INVENTION

The present invention offers a solution to the challenge of providing an application apparatus which, on the one hand, provides a great flexibility for placing in readiness for subsequent application the substances, which are composed of several components, and whereby the apparatus additionally makes possible the sequential application of the substances while, on the other hand, providing a fixed mixing relationship to the extent that this is required, as is a prerequisite, in particular, for the serial application of the mixing components.

The solution of the present invention offers the possibility to fixedly set the relationship between the amount of a firm or fixed reaction substance which is disposed on a support element, and the amount of a fluid in a fluid receptacle. In accordance with the present invention, the receptacle forms a grip, or at least the shaft of a grip, of a further support element which is in communication with an additional reaction substance or which can be brought into communication with such a reaction substance. This permits the application of the reaction substances one after another in a serial manner, whereby the possibility is offered to use a third reaction substance in the manner of a bundle.

It is to be understood that it is particularly advantageous if the first two reaction substances are selected such that their mixing relationship corresponds to the requirements of the task while, typically, the mixing relationship of the third component with respect to the pre-mixed mixture product formed by the mixing of the first and second components is not critical—that is, for example, its covering or layer thickness.

In an advantageous embodiment of the present invention, it is provided that the capability for inserting the receptacles into one another can be continued so that the required components can be held in readiness in their pre-prepared conditions in the desired serial application relationship. The dentist then merely pulls off each successively emptied receptacle and thereafter uses the next following receptacle.

The apparatus of the present invention thus offers the advantage of foregoing or omitting bundling without the need to forego the fixed mixing relationship—to the extent it is required—as is realized with single dose units.

In accordance with the present invention, it is advantageous that solid as well as fluid reaction substances are used. The fluid reaction substance can be a liquid but can also be a powder. A reaction substance as well as a double catalyzer system such as salt can be disposed on the end of the application element.

It is to be understood that the sealing between the cylinder and the receptacle can be provided in any desired suitable manner. It is particularly advantageous if the apparatus includes a piston having a conventional firm base. In connection with a suitable annular sealing, the apparatus of the present invention provides the ability to continue to function even if a considerably large pressure is applied which is the performance delivered by an application device which relies upon thin sheets or foils for separating the reaction substances from one another.

In accordance with the present invention, it is also advantageous if dry reaction substances are used which typically exhibit a particularly good stability. The apparatus of the present invention makes it possible to arrange, in desired combinations, an individual component or a plurality of components to be applied simultaneously—that is, in mixed condition—and to be applied one after another in a serial manner. In accordance with the present invention, it is particularly advantageous that the capability to insert the individual receptacles into one another at the same time ensures, as well, the sealing of each respective thereafter following component. This solution offers, to this extent, the dual function of, on the one hand, a grip for improved hand application and, on the other hand, an assurance that there is a sealing off of each respective component.

In an advantageous embodiment of the apparatus of the present invention, a stiffening tube is provided which stiffens or reinforces a plurality of receptacles which have been inserted into one another and which prevents an inadvertent loosening of the receptacles from one another. It is to be understood, that, in connection with correspondingly large overlapping areas between the shaft and the receptacles, a sufficient mechanical stability is, in any event, provided by such an arrangement whereby there is not the need for a corresponding stiffening tube.

In accordance with the present invention, the outwardly extending sealing and guiding surfaces can serve as the grip itself or the shaft can serve as the grip. The use of the shaft brings with it the advantage that the receptacles can have the same uniform outer diameter if they are cylindrically configured.

In one modification of the application device of the present invention, the receptacles are outwardly conically shaped, which facilitates the insertion of the receptacles into one another.

While it is possible to effect the sealing between the outer surfaces of the shaft and the inner surfaces of the receptacles by a type of surface sealing or, alternatively, by a labyrinth seal, it is preferred to provide an annular seal in the form of a sealing band. In this connection, an annular projection can be provided either on the interior side of the receptacles or on the outer side of the shaft which stands ready to function in the sealing operation. In a modified embodiment of the application device of the present invention, it is provided that a small sealing ring comprised of soft elastic material is disposed in the transition area between the shaft and the grip. In this configuration, it is advantageous if the inserted disposition of the receptacle is secured by a notch or detent element, in order to ensure a pressing of the receptacle edge on the sealing ring.

In accordance with the present invention, it is also advantageous that the application arrangement places in readiness a plurality of application elements. In this manner, it is also ensured that reaction substances of the type in which both components cannot be applied by the same applicator can be used, in the event that such reaction substances are specified for the task. An application of the components in a serial manner in which there is no possibility of exchange of the components can thus be ensured in this manner and undesired reactions of the components prior to their application can be avoided.

The application device of the present invention is not limited to only those applications in which dental material is applied. For example, other applications could include as well cleaning substances or the application of two adhesive components or additional applications including, for example, lacquer and, especially, repair lacquer for motor vehicles.

Further advantages, details and features of the present invention can be found in the following description of two embodiments of the application device of the present invention taken together with the schematic drawings, in which:

DETAILED DESCRIPTION OF THE PREFERRED EMBODIMENT

Figure 1:
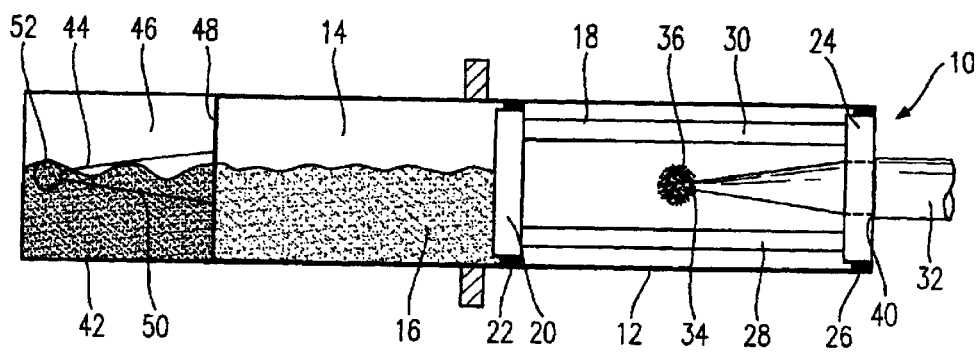
FIG. 1 is a schematic view of one embodiment of the application device of the present invention.

As seen in FIG. 1, one embodiment of the application device of the present invention, designated as the application device 10, includes a receptacle 12. The receptacle 12 receives in its interior space 14 a reaction substance 16 which, in the one embodiment illustrated in FIG. 1, is a fluid.

The receptacle 12 guides a piston 18 which is specially configured in accordance with the present invention. The piston 18 includes a piston base 20. The piston extends from approximately the middle of the cup-shaped receptacle 12 to the open end of the receptacle. In this position, the receptacle 12 includes an annular sealing projection 22 which is in contact with the piston base 20 and which presses against the piston base 20. The piston 18 further includes a piston cover 24 which is in contact with a further sealing projection 26 of the receptacle 12 at the open end thereof. Struts or braces 28, 30 extend between the piston base 20 and the piston cover 24, these struts permitting the entrance of fluid in a sidewise manner into the piston. To this extent, the side walls of the piston 18 or an insert in lieu of the piston include openings for the fluid.

A support or deposition element 32 is received through the piston cover 24, the support element 32 having on its working end 34 a reaction substance 36. The working end 34 can be configured in a conventional manner as a micro brush, a sponge, fabric or in any other desired suitable manner. The reaction substance 16 is preferably a salt, which is applied on the working end 34 by drying an appropriate carrier fluid which carries the salt on the working end 34. The support element 32 includes a recess 40 adjacent the piston cover 24 which prevents pressing in of the support element 32 beyond the position of the support element as shown in FIG. 1.

In the event that the substance to be applied has been made ready from the reaction substance 36, pressure is exerted on the support element 32. This effects movement of the piston 18 relative to the receptacle 12 in a manner in which the piston overcomes the sealing effect of the sealing projection 22. The fluid reaction substance 16 then flows into the region of the piston 18 and reacts with the reaction substance 36.

The application device shown in FIG. 1 further includes an outer receptacle 42 which receives a further reaction substance 44. The reaction substance 44 is, in any event, also a fluid in connection with the one embodiment of the application device shown in FIG. 1. An inner space 46 of the outer receptacle 42, which is cup-shaped, is closed off from the receptacle 12. The receptacle 12 includes a receptacle base 48. A further deposition or support element 50 is fixably secured to the receptacle base 48 centrally thereon. The support element 50 includes a working end 52 which is submerged in the reaction substance 44.

The outer receptacle 42 thus offers the possibility to support a further reaction substance 44 for subsequent mixing and application thereof which can be applied either before or after the composite substance comprised of the reaction substances 16 and 36.

Figure 2:
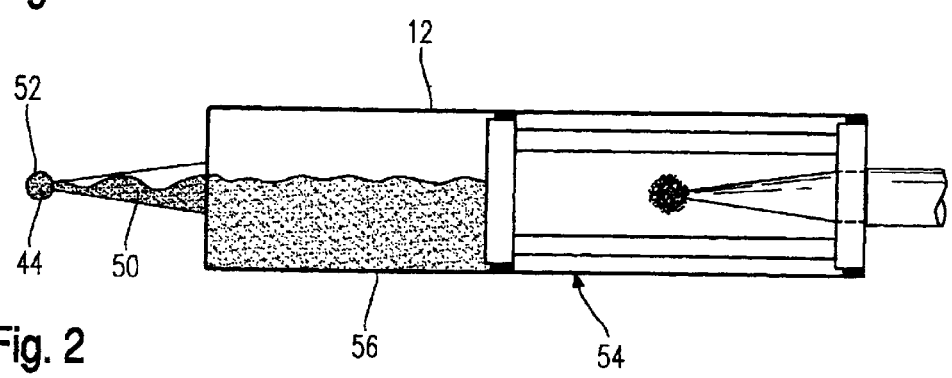
FIG. 2 is a schematic view of the application device shown in FIG. 1, whereby an outer receptacle has been removed and the application device is disposed for an application operation.

FIG. 2 shows the manner in which the application device can be deployed following the pulling off or removal of the outer receptacle 42. In this operational condition, the composite substance comprised of the reaction substances 16 and 36 has not yet been activated and the outer side 54 of the receptacle 12 serves as a grip for the support element 50 which supports, on its working end 52, the reaction substance 44. By repetitive submersion of the working end 52 in the interior space of the outer receptacle 42, additional charges of the further reaction substance 44 can be disposed onto the working end 52, in the event that the reaction substance 44 has been consumed by contact with the site which is to be treated. To this extent, the receptacle 12 with its outer surface 54 forms, at the same time, a grip 56 of a further support element 50.

Figure 3:
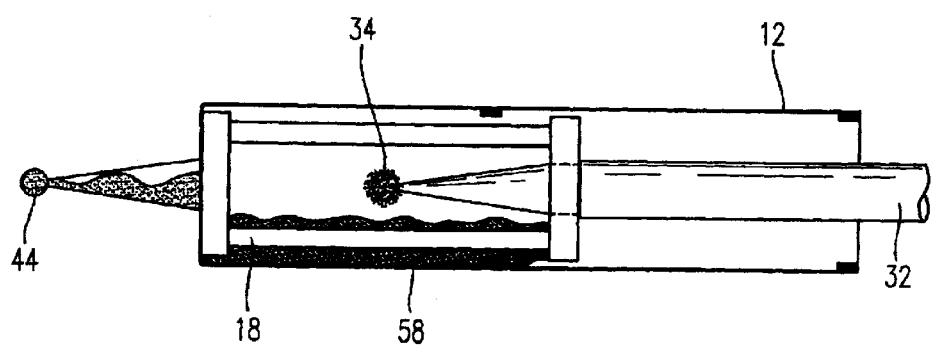
FIG. 3 is a schematic view of the application device shown in FIGS. 1 and 2 and showing the operation of the application device at an operational point at which a second substance is activated.

FIG. 3 shows the operational condition of the application device in which the reaction substance 16 has been combined with the reaction substance 36 to activate the composite substance. The piston 18, in this operational condition, is fully inserted into the receptacle 12 and the reaction substances 16 and 36 react with one another to form the composite substance 58. The withdrawal of the support element 32 out of the inner space of the piston 18 makes available the composite substance 58, which is disposed on the working end 34, for disposition thereof onto the site which is to receive the composite substance.

Figure 4:
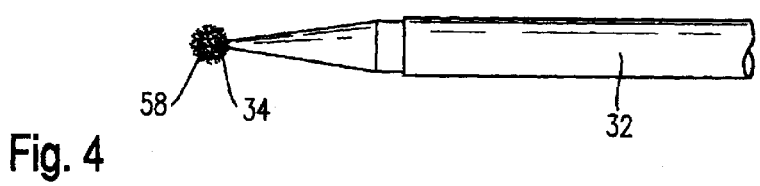
FIG. 4 is a schematic view of a support element of the application device shown in FIGS. 1–3 in which the second substance is supported in ready condition on the support element.

It is to be understood that, in this situation, two substances are disposed in a separated manner from one another. In accordance with the needs of the task, either the substance 58 or the substance 44 is initially applied to the site. FIG. 4 shows the support element 32 which has the composite substance 58 disposed on its working end 34.

Figure 5:
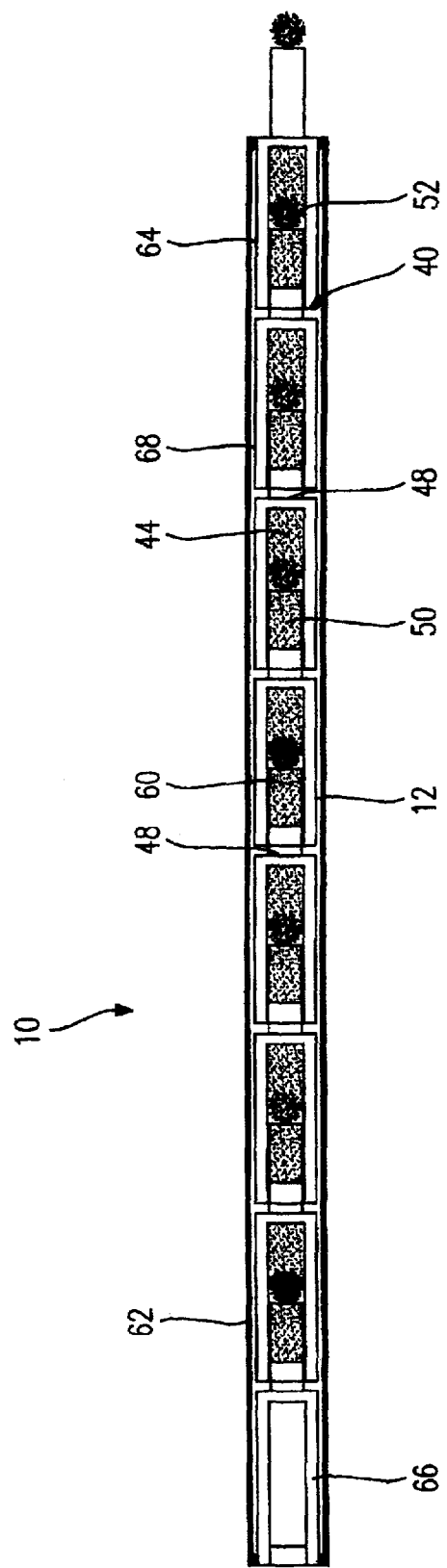
FIG. 5 is a schematic view of another embodiment of the application device of the present invention.

Another embodiment of the application device of the present invention 10 is shown in FIG. 5. In this embodiment, a plurality of receptacles 12 are provided in a condition in which the receptacles are inserted into one another and a total of eight such receptacles are so arranged with one another in this embodiment of the application device. This embodiment of the application device is configured for the sequential or serial application of substances. In this connection, each receptacle receives in its inner space 46 a reaction substance 44. A support element 50 is submerged in the inner space and is formed on the end of a substantially thick shaft 60. The support element 50 includes a working end 52 which is wetted with the reaction substance 44. The support element 50 is connected with the base 48 of the next following receptacle 12, which itself receives the support element 50 of the thereafter next following receptacle 12.

The inserted length of the support element can be accommodated to a wide range of requirements. Preferably, the diameter of the shaft 60 is dimensioned in correspondence with the inner diameter of the receptacle 12 and extends approximately to one-half the length of the receptacle 12. In this connection, there is produced a substantially stable positioning of the receptacle interior including, as well, when the receptacle is in its inserted condition. A seal between the shaft 60 and the receptacle 12 can be provided in any suitable desired manner. For example, each receptacle 12 can support on its open end a seal projection such as, for example, the projection 40 provided on the support element.

In the embodiment illustrated in FIG. 5, it can be seen that there is a multiple arrangement of the receptacles 12, whose stiffness or rigidity is promoted by a stiffened or more rigid condition by a pipe or tube 62 disposed therearound.

The activation of the substance contained in the first receptacle 64 is effected by the brief withdrawal of the receptacle 64 from the stiffening tube 62 and the insertion thereof into the last receptacle 66. By the application of pressure on the open backside of the cup-shaped receptacle 64, the arrangement of the receptacles inserted into one another in the stiffening tube 62 is pushed forward to an extent such that the working end 52 of the second receptacle 68 extends sufficiently out of the tube 62 in order to effect an application of the reaction substance 44 carried on the working end 52 onto the site to be handled.

It is to be understood that the sequential arrangement and application of the reaction substances in the receptacles can be reconfigured or transformed in consideration of the respective application scenario. For example, two reaction substances can be provided in the receptacles in an alternating manner such that the required substances automatically follow one another in their application sequence.

The present invention is, of course, in no way restricted to the specific disclosure of the specification and drawings, but also encompasses any modifications within the scope of the appended claims.

What is claimed is:

1. An application device for applying a composite substance onto a site, the composite substance being formed of at least two reaction substances which react with one another, comprising:

a receptacle having a portion for receiving a first reaction substance, a support element carried by the receptacle, the support element having a working end which carries a second reaction substance, the receptacle being operable to guide the working end of the support element so that the second reaction substance comes into reaction contact with the first reaction substance enclosed by the receiving portion of the receptacle to thereby effect the formation of the composite substance, the application device being characterized by a plurality of receptacles insertable into one another, whereby each receptacle includes a support element which extends into the neighboring receptacle.

2. The application device for applying a composite substance onto a site as set forth in claim 1, further being characterized by a piston disposed in the receptacle adjacent the first reaction substance but which is insertable under pressure into the first reaction substance receiving portion of the receptacle, whereby, in the inserted condition of the piston, a fluid connection is established between the first and second reaction substances.

3. The application device for applying a composite substance onto a site, as set forth in claim 1, wherein the receptacle guides a piston, which has a hollow interior dimensioned for receiving the support element inserted therein.

4. The application device for applying a composite substance onto a site as set forth in claim 1, further being characterized by a piston which is slidable within the receptacle and an annular projection which seals against the base of the piston in the non-activated position of the piston and, in connection with a sliding movement of the piston from its non-activated position into its activated position, a gap, especially, an annular gap, is formed which permits the spillover of fluids into the interior space of the piston.

5. An application device for applying a composite substance onto a site, the composite substance being formed of at least two reaction substances which react with one another, comprising:

a receptacle having a portion for receiving a first reaction substance, a support element carried by the receptacle, the support element having a working end which carries a second reaction substance, the receptacle being operable to guide the working end of the support element so that the second reaction substance comes into reaction contact with the first reaction substance enclosed by the receiving portion of the receptacle to thereby effect the formation of the composite substance, an outer receptacle into which the receptacle is inserted and having a base, the outer receptacle having an inner space sealed off by the receptacle base of the outer receptacle and receiving a further fluid, and the receptacle base having a further support element.

6. An application device for applying a composite substance onto a site, the composite substance being formed of at least two reaction substances which react with one another, comprising:

a receptacle having a portion for receiving a first reaction substance, a support element carried by the receptacle, the support element having a working end which carries a second reaction substance, the receptacle being operable to guide the working end of the support element so that the second reaction substance comes into reaction contact with the first reaction substance enclosed by the receiving portion of the receptacle to thereby effect the formation of the composite substance, characterized by a plurality of receptacles being disposed in inserted condition with one another and being enclosed in a tube which promotes stiffening of the inserted receptacle arrangement.

7. An application device according to claim 6, wherein the receptacles are insertable in one another and are of uniform size within the tube, a first receptacle of the arrangement is insertable into a last receptacle and the arrangement of the receptacles which are in inserted condition with one another is displaceable relative to the tube while being guided therethrough.

* * * * *